(12) United States Patent
Choi et al.

(10) Patent No.: US 8,993,474 B2
(45) Date of Patent: Mar. 31, 2015

(54) DEHYDROGENATION CATALYST

(75) Inventors: Jin Soon Choi, Anyang-si (KR); Won Il Kim, Seongnam-si (KR); Hyong Lim Koh, Seoul (KR); Young Gyo Choi, Yongin-si (KR)

(73) Assignee: Hyosung Corporation, Seoul (KR)

( * ) Notice: Subject to any disclaimer, the term of this patent is extended or adjusted under 35 U.S.C. 154(b) by 27 days.

(21) Appl. No.: 13/142,506

(22) PCT Filed: May 25, 2009

(86) PCT No.: PCT/KR2009/002739
§ 371 (c)(1),
(2), (4) Date: Jun. 29, 2011

(87) PCT Pub. No.: WO2010/076928
PCT Pub. Date: Jul. 8, 2010

(65) Prior Publication Data
US 2011/0263416 A1 Oct. 27, 2011

(30) Foreign Application Priority Data
Dec. 30, 2008 (KR) .......... 10-2008-0136737

(51) Int. Cl.
*B01J 27/13* (2006.01)
*B01J 35/10* (2006.01)
(Continued)

(52) U.S. Cl.
CPC ............. *B01J 23/6562* (2013.01); *B01J 23/58* (2013.01); *B01J 23/60* (2013.01); *B01J 23/62* (2013.01); *B01J 23/626* (2013.01); *B01J 35/002* (2013.01); *B01J 35/1014* (2013.01); *B01J 35/1019* (2013.01); *B01J 35/1042* (2013.01); *B01J 35/1061* (2013.01); *B01J 35/1066* (2013.01); *B01J 35/1071* (2013.01); *B01J 35/1076* (2013.01); *B01J 35/108* (2013.01);
(Continued)

(58) Field of Classification Search
CPC ............ B01J 23/58; B01J 23/60; B01J 23/62; B01J 23/626; B01J 23/6562; B01J 35/1061; B01J 35/1066; B01J 35/1071; B01J 35/1076; B01J 35/1042
USPC ......................... 502/213, 226, 227, 229, 230
See application file for complete search history.

(56) References Cited

U.S. PATENT DOCUMENTS 4,902,848 A  2/1990 Scott et al.
4,914,075 A * 4/1990 Bricker et al. ............... 502/330
(Continued)

OTHER PUBLICATIONS

Machine translation of JP07-194974.*
(Continued)

*Primary Examiner* — Jun Li
(74) *Attorney, Agent, or Firm* — Lucas & Mercanti, LLP

(57) ABSTRACT

This invention relates to a dehydrogenation catalyst having a macropore size and a high active density of platinum, suitable for use in dehydrogenation of a hydrocarbon gas. This dehydrogenation catalyst having a macropore size and a high active density of platinum is highly active, has high active density per unit catalytic surface area, facilitates material transfer of reactants and products, delays deactivation due to coke formation, keeps the initial activity constant after being regenerated thanks to the disposal of coke, has high strength and so is resistant to external impact, and undergoes neither structural changes due to heat nor changes in the properties of active materials.

8 Claims, 3 Drawing Sheets

(51) Int. Cl.
  *B01J 27/185* (2006.01)
  *B01J 27/138* (2006.01)
  *B01J 27/135* (2006.01)
  *B01J 23/656* (2006.01)
  *B01J 23/58* (2006.01)
  *B01J 23/60* (2006.01)
  *B01J 23/62* (2006.01)
  *B01J 35/00* (2006.01)
  *B01J 37/02* (2006.01)
  *C07C 5/333* (2006.01)

(52) U.S. Cl.
  CPC ............ *B01J37/0207* (2013.01); *C07C 5/333* (2013.01); *C07C 5/3337* (2013.01); *C07C 2521/04* (2013.01); *C07C 2521/08* (2013.01); *C07C 2521/12* (2013.01); *C07C 2523/42* (2013.01); *C07C 2523/58* (2013.01); *C07C 2523/60* (2013.01); *C07C 2523/62* (2013.01); *C07C 2527/10* (2013.01); *C07C 2527/12* (2013.01); *C07C 2527/14* (2013.01)

USPC .......... 502/213; 502/226; 502/227; 502/229; 502/230

(56) References Cited

U.S. PATENT DOCUMENTS

| | | | |
|---|---|---|---|
| 5,321,192 A | 6/1994 | Cottrell et al. | |
| 5,358,920 A * | 10/1994 | Ma et al. | 502/330 |
| 6,162,758 A * | 12/2000 | Brocker et al. | 502/340 |
| 2002/0022755 A1* | 2/2002 | Dongara et al. | 585/661 |
| 2005/0033101 A1* | 2/2005 | Voskoboynikov et al. | 585/660 |
| 2006/0067877 A1* | 3/2006 | Revel et al. | 423/628 |
| 2008/0051618 A1* | 2/2008 | Kim et al. | 585/431 |
| 2010/0087694 A1* | 4/2010 | Mishima | 585/661 |

OTHER PUBLICATIONS

International Search Report PCT/KR2009/002739 dated Jan. 25, 2010.

* cited by examiner

Cat. B

Cat. D

Cat. E

DEHYDROGENATION CATALYST

TECHNICAL FIELD

The present invention relates to a dehydrogenation catalyst having a macropore size and a high active density of platinum, suitable for use in dehydrogenation of a hydrocarbon gas.

BACKGROUND ART

Dehydrogenation of hydrocarbon gases is carried out at a high temperature of at least 550° C. Because the catalytic reaction occurs at high temperature, it is accompanied by side reactions such as thermal decomposition and coke formation. The extent of such side reactions acts as an important factor that determines the selectivity and the activity of catalyst. Among the side reactions, the coke formation reaction causes the catalytic active material to be covered with coke which prevents contact with a reactant, undesirably decreasing the total reaction conversion. Furthermore, as the coke formation progresses, the inlets of pores of the catalyst are blocked, so that the active material present in the pores is rendered useless, drastically accelerating the deactivation of the catalyst.

In addition, the dehydrogenation catalyst for the hydrocarbons is required to be thermally stable. Because of the high reaction temperature and heat generated during the regeneration of coked catalyst, thermal deformation of catalyst itself and structural sintering may result, thus causing changes in the catalytic reactivity. For this reason, structural compatibility of the catalyst, thermal stability of catalyst structure, thermal stability of an active component, and regeneration of the coked catalyst are regarded as important when making the determination of a superior catalyst.

Typically, dehydrogenation catalysts are classified into chromium oxide catalysts and platinum catalysts.

In a chromium-based catalyst (U.S. Pat. No. 6,797,850), the deactivation rate of the catalyst is fast attributed to coke formation and thus the regeneration rate is also fast, so that the lifetime of the catalyst is shorter than that of a platinum-based catalyst, and there are problems due to the toxicity of chromium itself.

Exemplary platinum-based catalysts are a catalyst having an outer layer containing an active component of 40~160 μm, and a layered catalyst including gamma-alumina (U.S. Pat. No. 6,756,515) or alpha-alumina (U.S. Pat. No. 6,486,370) as an inner layer, but the inner layer that defines the specific surface area of the catalyst by pores has no metal active component resulting in low dispersibility and low active area. Furthermore, when gamma-alumina is used, side reactions may increase due to acid sites of alumina itself, and changes in structural properties in which alumina crystallinity changes and the specific surface area decreases may take place during the reaction. On the other hand, alpha-alumina may decrease dispersibility of noble metals due to the low specific surface area and may reduce the entire active area of a noble metal, leading to low catalytic activity.

For the preparation of catalysts, there is a disclosed a platinum-based catalyst having no chlorine which is applied to the dehydrogenation of ethane (U.S. Pat. No. 7,375,049). When chlorine is not contained in this way, initial activity of the reaction may be high. However, in the case where this catalyst is used for a long period of time to carry out the process, the active metal component may be sintered, and thus dispersibility may decrease, undesirably deteriorating catalytic activity (Catalysis Today 111 (2006) 133-139).

The platinum-based catalysts are prepared using silica (U.S. Pat. No. 7,432,406), zeolite or boron silicate (U.S. Pat. No. 6,555,724) as a carrier thereof, but these catalysts are composed mainly of pores having an average pore diameter of 10 nm or less, and thereby very sensitively acts for structural closure attributed to coke formation, undesirably drastically deactivating the catalyst.

Conventional dehydrogenation catalyst related patents include contents regarding kinds of active components and carriers of catalysts, and pore distribution which is one of the physical properties of catalysts has not yet been introduced. The pore volume and the pore size are important factors that determine the material transfer coefficient of reactants and products, and the diffusion resistance of a material under conditions of a rapid chemical reaction rate determines the total reaction rate, and thus a structure having large pores may be favorable in terms of keeping the activity of the catalyst high, and the use of a carrier having a large pore size makes it difficult to stack coke and is thus favorable in maintaining the activity of the catalyst.

Therefore, the development of a dehydrogenation catalyst having a macropore size and being superior in activity, selectivity and coke stability is required.

DISCLOSURE

Technical Problem

The present inventors have studied dehydrogenation catalysts having a macropore size and high activity, selectivity and coke stability and discovered the fact that a dehydrogenation catalyst having a macropore size and a high active density of platinum may be prepared using a thermally deformed alumina carrier using room temperature/high temperature adsorption, and also dehydrogenation of propane using the catalyst thus prepared may result in high conversion, selectivity, and yield, thereby completing the present invention.

Technical Solution

The present invention is intended to provide a dehydrogenation catalyst having a macropore size and a high active density of platinum, suitable for use in the dehydrogenation of a hydrocarbon gas.

BEST MODE

Figure 1:
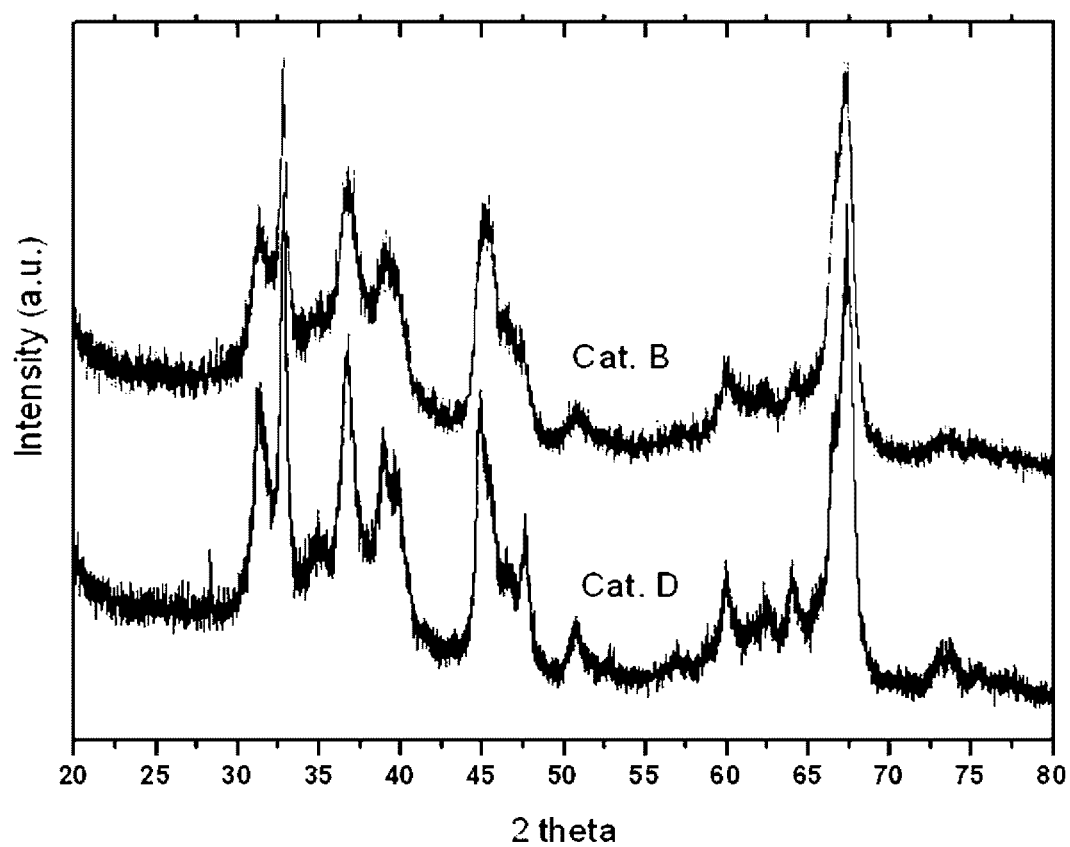
FIG. 1 shows results of measuring crystallinity of alumina of catalysts B and D according to the present invention using X-ray analysis.

The present invention provides a dehydrogenation catalyst, suitable for use in the dehydrogenation of a hydrocarbon gas, which comprises platinum, an assistant metal, an alkali metal or alkaline earth metal, and a halogen component, which are supported on a carrier, wherein the carrier has mesopores of 5~100 nm and macropores of 0.1~20 μm, and an active density of platinum is 0.001~0.009 wt %/m$^2$.

The hydrocarbon is a $C_2$~$C_5$ linear hydrocarbon or ethylbenzene.

Hereinafter, the present invention is described in detail.

According to the present invention, the dehydrogenation catalyst comprises based on the total weight of the catalyst, 0.05~1.5 wt % of platinum, 0 05~2.0 wt % of the assistant metal, 0.05~3.0 wt % of the alkali metal or alkaline earth metal, and 0.1~3.0 wt % of the halogen component, which are supported on the carrier using room temperature/high temperature adsorption.

Platinum is used as a main metal, and the assistant metal is selected from the group consisting of tin, germanium, gallium, indium, zinc, and manganese. Particularly useful is tin. The alkali metal or alkaline earth metal is selected from the group consisting of calcium, potassium, sodium, magnesium, lithium, strontium, barium, radium, and beryllium. The halogen component is selected from the group consisting of chlorine, phosphorus, and fluorine, and chlorine is particularly useful.

In the catalyst according to the present invention, the carrier may include alumina, silica, and a mixture thereof. Particularly useful is alumina. The theta crystallinity of alumina is a factor that determines the degree of coke formation, and may be set to 90% or more.

The carrier has a specific surface area of 50~170 m$^2$/g, and includes mesopores of 5~100 nm and macropores of 0.1~20 μm. If the specific surface area of the carrier is less than 50 m$^2$/g, the dispersibility of a metal active component may decrease. In contrast, if the specific surface area thereof exceeds 170 m$^2$/g, gamma-crystallinity of alumina may be kept high and side reactions may thus increase. Furthermore, the pore volume and the pore size of the carrier are main factors that determine the material transfer coefficient of reactants and products. Also because the diffusion resistance of a material under conditions of a rapid chemical reaction rate determines the total reaction rate, a structure having large pores is favorable in terms of keeping the activity of the catalyst high. Hence, the use of a carrier having large pores makes it difficult to stack coke and increases a material transfer rate, and thus even when a liquid hourly space velocity (LHSV) is increased, high reactive activity may result. If the pores of the carrier are less than 5 nm, the material transfer rate may be lowered by Knudsen diffusion. In contrast, if the pores of the carrier are larger than 20 μm, the strength of the carrier may be lowered. Specifically, because of Knudsen diffusion at a pore size of 10 nm or less, transition diffusion at a pore size of 10~1000 nm and bulk diffusion at a pore size of 1000 nm or more, the use of macropores of 1 μm or more may exhibit a material transfer rate 20 times or greater than that compared to when using pores of 10 nm ("Heterogeneous Catalysis In Practice," Charles N. Satterfield, p. 334-344 (1980) McGraw-Hill).

The dehydrogenation catalyst according to the present invention has high dispersibility of platinum, and the active density of platinum acting as an active site may be 0.001~0.009 wt %/m$^2$. If the active density of platinum is less than 0.001 wt %/m$^2$, active sites are not sufficient and thus the reaction conversion may decrease. In contrast, if the active density thereof exceeds 0.009 wt %/m$^2$, the dispersibility of platinum may decrease and thus coke formation may increase, and side reactions may increase and thus reaction selectivity may decrease. The active density of platinum is an important factor that determines the particle size. The distribution of the corner, edge, and planar faces varies depending on the size of platinum particles, and is directly related to the reaction conversion and the selectivity. In the case where the platinum particles have a size of 1.35 nm, a 50% corner may be provided. In contrast, if the particle size is 2.15 nm, 18% corner, 45% edge, and 37% plane face may result. If the size of the particles is 5.1 nm, 3% corner, 27% edge, and 70% plane face are obtained, so that the properties thereof may change, thus causing changes in the conversion and the selectivity in the catalytic reaction ("Catalyst Preparation", John Regalbuto, p. 422-448 (2006) CRC Press).

The catalyst according to the present invention may be prepared by controlling the amount of the halogen component to 0.1~3.0 wt % based on the total weight thereof. If the amount of the halogen is less than 0.1 wt %, the rate of coke formation may rapidly increase in the catalyst, and the regeneration of the coked catalyst may decrease and the dispersibility of platinum may be lowered upon regenerating the catalyst. In contrast, if the amount of the halogen exceeds 3.0 wt %, the activity of the catalyst may decrease due to poisoning of the noble metal by the halogen. Specifically, the halogen component, in particular, chlorine, binds to the aluminum element of the alumina carrier, so that the properties of the Lewis acid of alumina itself decrease, making it easy to desorb a product, thereby suppressing coke formation. As such, the coke may be formed in such a way that the reaction is completed with coke adsorbed on the carrier itself or the main product/byproduct formed at the active sites may be spilt-over and stacked on the carrier and additional coke formation reactions occur. However, when the Lewis acid is weakened to facilitate desorption of product, the amount of coke stacked on the carrier may be decreased, thus reducing coke formation. Also, even when the phase of alumina is transformed from gamma into theta or alpha so that the acid sites of crystalline alumina itself are decreased, the same effects of reducing acid sites may manifest themselves. Moreover, chlorine is utilized to control the sintering of platinum during the regeneration of the catalyst ("Reactivation of sintered Pt/Al$_2$O$_3$ oxidation catalysts" F. Cabello Galisteo et al., Appl. Catal. B 59 (2005) 227-233).

The catalyst according to the present invention may have a bulk density of 0.5~0.8 g/cc. The bulk density of the catalyst determines the amount of packed catalyst in the process, thus setting the total active density of the catalyst fed in the process.

The catalyst according to the present invention may have a strength of 15~70 N, and has to have a high strength so that it is rigid even when regenerated or circulated. If the strength of the catalyst is below 15 N, it may easily break down, making it difficult to apply to a continuous reaction system. Because the reaction of the dehydrogenation catalyst is accompanied by coke formation, it is regenerated by burning coke via oxidation after a predetermined reaction. During this process, thermal breakage may occur. When the catalyst circulates in order to operate, friction or impact may be applied thereto upon transport. In the case where a catalyst weak to impact is used, it hinders the flow of the product and increases the inner pressure of the reactor, undesirably lowering the conversion of the catalyst. Hence, the catalyst having high strength is very advantageous in terms of process operation.

The dehydrogenation catalyst according to the present invention has a macropore size and a high active density of platinum, and thereby is highly active, has high active density per unit catalytic surface area, facilitates the material transfer of reactants and products, delays deactivation due to coke formation, keeps the initial activity constant after being regenerated thanks to the disposal of coke, has high strength and so is resistant to external impact, and undergoes neither structural changes due to heat nor changes in the properties of active materials.

Mode for Invention

A better understanding of the present invention is furnished by the following examples which are set forth to illustrate, but are not to be construed as limiting the present invention.

Example 1

Preparation of Dehydrogenation Catalyst

Alumina having spherical gamma-crystallinity prepared according to U.S. Pat. No. 4,542,113 was purchased from Sasol, Germany, and was thermally deformed using a tube electric furnace (available from Korea Furnace) under a stream of air of 300 mL/min at 1050° C. for 6 hours and then used as a carrier for a catalyst. The crystallinity of alumina was measured using X-ray analysis. The results are shown in FIG. 1, with a theta crystallinity of 90% or more.

Using the thermally deformed alumina carrier, a catalyst was prepared via room temperature/high temperature adsorption. Specifically, 0.0717 g of tin chloride ($SnCl_2$, >99%, Sigma), 0.5714 g of hydrochloric acid (HCl, >35%, JUNSEI), and 0.0714 g of nitric acid ($HNO_3$, 70%, Yakuri) were dissolved in 24 g of distilled water, and then supported on 20 g of the thermally deformed alumina. The supported solution was dried using a rotary evaporator (HAHNSHIN Scientific Co.), stirred at room temperature for 1.5 hours at 25 rpm, and rotated under reduced pressure at 80° C. for 1.5 hours at 25 rpm and thus dried. In order to completely dry it, it was dried in an oven at 105° C. for 15 hours, and thermally treated in a heating furnace at 700° C. for 3 hours. Subsequently, 15 g of the tin-supported alumina was added to a solution of 0.3319 g of chloroplatinic acid ($H_2PtCl_6.6H_2O$, 99.95%, Aldrich), 0.2143 g of hydrochloric acid, and 0.0536 g of nitric acid in 18.0552 g of distilled water so that they were supported on the alumina. The supported solution was dried using a rotary evaporator, stirred at room temperature for 1.5 hours at 25 rpm, and rotated under reduced pressure at 80° C. for 1.5 hours at 25 rpm and thus dried, further dried in an oven at 105° C. for 15 hours, and thermally treated in a heating furnace at 600° C. for 3 hours. Subsequently, supported on 10 g of the tin/platinum-supported alumina was a solution of 0.1933 g of potassium nitrate ($KNO_3$, >99%, Sigma-Aldrich) and 0.1629 g of hydrochloric acid in 12.1136 g of distilled water. The supported solution was dried using a rotary evaporator, stirred at room temperature for 1.5 hours at 25 rpm, and rotated under reduced pressure at 80° C. for 1.5 hours at 25 rpm and thus dried, further dried in an oven at 105° C. for 15 hours, and thermally treated in a heating furnace at 600° C. for 3 hours, thus preparing a dehydrogenation catalyst.

Catalysts A, B and C were obtained by means of the above preparation method using alumina having different physical properties (specific surface area, pore volume, strength) as shown in Table 1 below. The specific surface area and the pore volume of the catalysts A, B and C were directly proportional, and the pore volume and the strength of the catalyst were inversely proportional thereto.

TABLE 1

Physical Properties of Alumina Carrier
(Specific Surface Area, Pore Volume, Strength)

| Carrier | Catalyst A | Catalyst B | Catalyst C |
| --- | --- | --- | --- |
| Specific Surface Area ($m^2/g$) | 96 | 124 | 150 |
| Pore Volume (cc/g) | 0.34 | 0.70 | 0.86 |
| Strength (N) | 48 | 31 | 15 |

Example 2

Preparation of Dehydrogenation Catalyst

Alumina before thermal deformation used for preparing the catalyst B of Example 1 was thermally deformed at 1100° C. for 6 hours under stream of air of 300 mL/min using a tube electric furnace and then used as a carrier for the catalyst. The crystallinity of alumina was measured using X-ray analysis. The results are shown in FIG. 1, with a theta crystallinity of 90% or more.

A catalyst D was obtained using the thermally deformed alumina carrier in the same manner as in Example 1.

Comparative Example 1

Preparation of Dehydrogenation Catalyst Using Carrier Having No Macropores

A catalyst E was prepared via thermal treatment and supporting of active components in the same manner as in Example 1, with the exception that a carrier having no macropores unlike the alumina carrier of Example 1 was used.

Test Example 1

Evaluation of Activity of Dehydrogenation Catalyst

The activities of the catalysts B, D and E of Examples 1~2 and Comparative Example 1 were evaluated. The results are shown in Table 2 below. The results of observing cross-sections of the catalysts B, D and E using SEM are shown in FIG. 2.

TABLE 2

| | Catalyst B | Catalyst D | Catalyst E |
| --- | --- | --- | --- |
| Cl Content (wt %) | 1.12 | 0.94 | 1.15 |
| Mesopore Volume (cc/g) | 0.47 | 0.32 | 0.58 |
| Macropore Volume (cc/g) | 0.23 | 0.25 | — |
| Strength (N) | 31 | 38 | 29 |
| Pt Active Density (wt %/$m^2$) | 0.0036 | 0.0048 | 0.0054 |
| Bulk Density (g/cc) | 0.63 | 0.70 | 0.59 |

Figure 2:
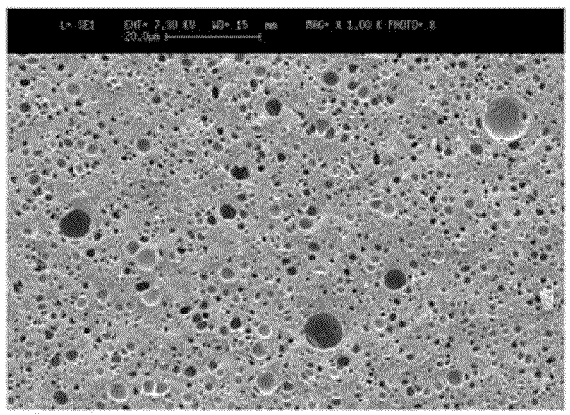
FIG. 2 shows scanning electron microscope (SEM) images of the cross-sections of the catalysts B and D according to the present invention.
Figure 2:
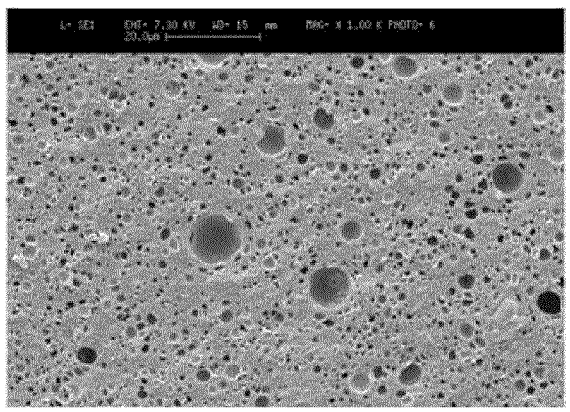
Figure 2:
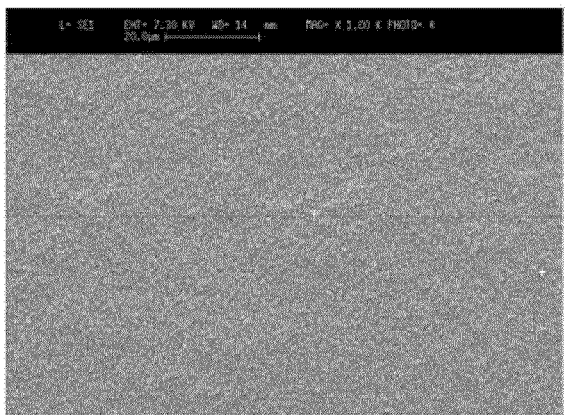

As is apparent from Table 2 and FIG. 2, the catalysts B and D had well-developed macropores, high strength, high Pt active density per unit area, and high bulk density. Whereas, the catalyst E had smaller pore volume and lower strength than the catalyst B, and high pore structure was not observed therein.

Test Example 2

Test of Performance of Dehydrogenation Catalyst

In order to evaluate the performance of the dehydrogenation catalyst according to the present invention, the following test was performed.

A quartz reactor having a volume of 7 mL was packed with 3.2 mL of each of the catalysts B, D of Examples 1 and 2 and the catalyst E, after which a gas mixture of propane and hydrogen was fed thereto so that dehydrogenation was carried out. As such, the ratio of hydrogen and propane was set to 1:1, and the reaction temperature was 620° C. under adiabatic conditions, the absolute pressure was 1.5 atm, and the LHSV was 15 hr$^{-1}$. After the reaction, the gas composition was analyzed using a gas chromatograph (GC) connected to the reactor, and the propane conversion and the selectivity for propylene in the reaction product were determined.

Figure 3:
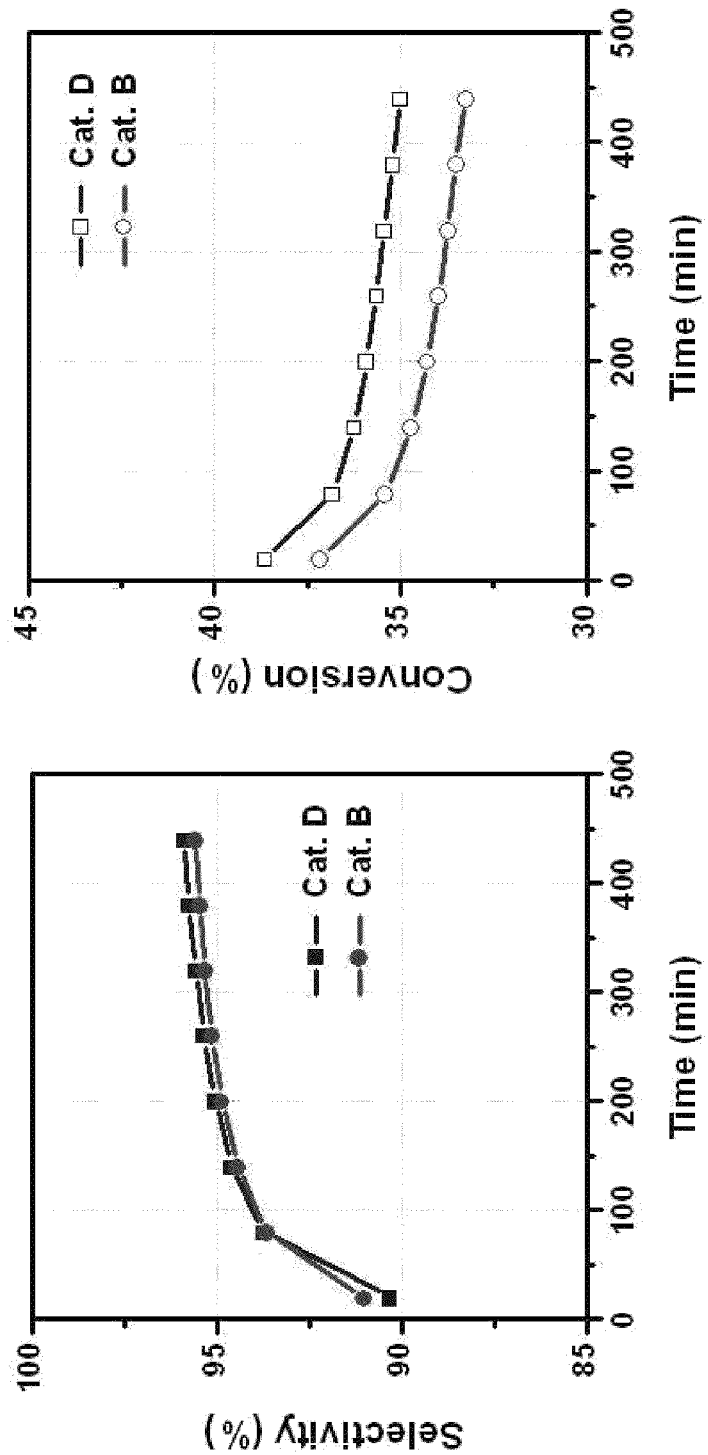
FIG. 3 shows the propane conversion and the selectivity for propylene in a reaction product, as analyzed using gas chromatography after dehydrogenating propane using the catalysts B and D according to the present invention.

The results are shown in FIG. 3.

As shown in FIG. 3, the catalyst D according to the present invention having high dispersibility exhibited superior reaction selectivity, and increased propane conversion thanks to the increased active density of platinum. The average amounts of coke formed for 8 hours in the catalysts B, D and E were respectively 0.328%/hr, 0.251%/hr and 0.355%/hr.

Test Example 3

Test of Performance of Dehydrogenation Catalyst at Different LHSVs and Pt Active Densities Dehydrogenation was carried out in the same manner as in Test Example 2, with the exception that LHSV was maintained at 10 hr$^{-1}$ and 20 hr$^{-1}$ using the catalyst B. After the reaction, the gas composition was analyzed using GC connected to the reactor, and the propane conversion and the propylene yield were determined.

The results are shown in Table 3 below.

unit catalytic surface area, facilitates the material transfer of reactants and products, can delay deactivation due to coke formation, keeps the initial activity constant after being regenerated thanks to the disposal of coke, has high strength and so is resistant to external impact, and undergoes neither structural changes due to heat nor changes in the properties of active materials.

We claim:

1. A dehydrogenation catalyst for use in dehydrogenation of a hydrocarbon gas, comprising
   platinum,
   an assistant metal,
   an alkali metal or alkaline earth metal,
   and a halogen component, which are supported on a carrier, wherein
   the carrier is alumina having a theta cryslallinity of 90% or more, and having mesopores of 5~100 nm and macropores of 0.1~20 μm, and having mesoporc volume of 0.32 -0.47 cc/g and macropore volume of 0.23-0.25 cc/g, and
   the platinum has an active density of 0.001-0.009 wt %/m$^2$ and a strength of 15-70 N.

2. The dehydrogenation catalyst of claim 1, wherein the catalyst is capable of dehydrogenating a hydrocarbon is a $C_2$-$C_5$ linear hydrocarbon or ethylbenzene.

3. The dehydrogenation catalyst of claim 1, comprising 0.05~1.5 wt % of platinum, 0.05~2.0 wt % of the assistant metal, 0.05~3.0 wt % of the alkali metal or alkaline earth metal, and 0.1~3.0 wt % of the halogen component, based on total weight of the catalyst, which are supported on the carrier.

TABLE 3

| | Reaction Time | | | | | | | |
|---|---|---|---|---|---|---|---|---|
| | 1 hr | | 5 hr | | 10 hr | | 20 hr | |
| LHSV | Conversion (wt %) | Yield (wt %) | Conversion (wt %) | Yield (wt %) | Conversion (wt %) | Yield (wt %) | Conversion (wt %) | Yield (wt %) |
| Catalyst E (15 hr$^{-1}$) | 31.8 | 30.4 | 29.6 | 28.3 | 28.2 | 27.0 | 26.6 | 25.4 |
| Catalyst B (10 hr$^{-1}$) | 39.9 | 36.3 | 37.9 | 35.1 | 36.7 | 34.2 | 35.1 | 32.8 |
| Catalyst B (20 hr$^{-1}$) | 36.4 | 34.2 | 34.2 | 32.5 | 32.4 | 30.9 | 30.3 | 29.0 |

As is apparent from Table 3, the catalyst B according to the present invention had a Pt active density of 0.0036 wt %/m$^2$, and the catalyst E had a Pt active density of 0.0054 wt %/m$^2$ (Table 2). Despite the Pt active density of the catalyst E being higher, the catalyst E had lower propane conversion and propylene yield, and thus low activity. The yield of the catalyst E upon dehydrogenation at LHSV of 15 hr$^{-1}$ was lower than the yield of the catalyst B upon dehydrogenation at LHSV of 20 hr$^{-1}$. This is considered to be because the catalyst according to the present invention includes macropores and thus the activity thereof is higher.

INDUSTRIAL APPLICABILITY

According to the present invention, a dehydrogenation catalyst has a macropore size and a high active density of platinum, and is thus highly active, has high active density per 4. The dehydrogenation catalyst of claim 1, wherein the assistant metal is one or more selected from the group consisting of tin, germanium, gallium, indium, zinc, and manganese.

5. The dehydrogenation catalyst of claim 1, wherein the alkali metal or alkaline earth metal is one or more selected from the group consisting of calcium, potassium, sodium, magnesium, lithium, strontium, barium, radium, and beryllium.

6. The dehydrogenation catalyst of claim 1, wherein the halogen component is one or more selected from the group consisting of chlorine, and fluorine.

7. The dehydrogenation catalyst of claim 1, wherein the carrier has a specific surface area of 50~170 m$^2$/g.

8. The dehydrogenation catalyst of claim 1, wherein the catalyst has a bulk density of 0.5-0.8 g/cc.

* * * * *